Figure 1:
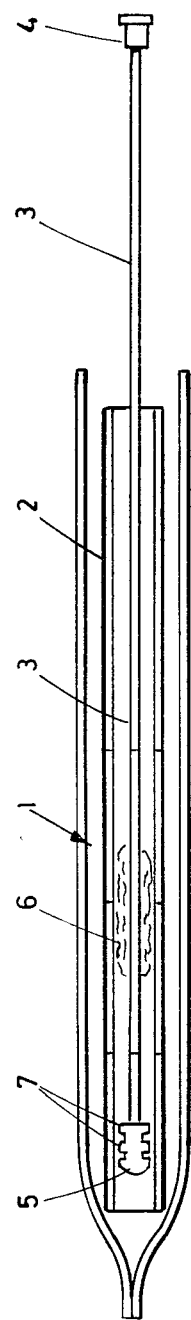

United States Patent [19]

Nydahl et al.

[11] Patent Number: 4,562,847
[45] Date of Patent: Jan. 7, 1986

[54] INSTRUMENT FOR OBTAINING SAMPLES FROM UTERUS OF ANIMALS

[75] Inventors: Claes Nydahl, Nya Välsätravägen 19, S-752 46 Uppsala, Sweden; Odd Knudsen, Uppsala, Sweden

[73] Assignee: Claes Nydahl, Uppsala, Sweden

[21] Appl. No.: 466,028

[22] Filed: Feb. 14, 1983

[30] Foreign Application Priority Data

Feb. 18, 1982 [SE] Sweden ............................. 8201017

[51] Int. Cl.⁴ ............................................. A61B 10/00
[52] U.S. Cl. ................................... 128/757; 128/749
[58] Field of Search ............... 128/749, 757, 758, 304, 128/759

[56] References Cited

U.S. PATENT DOCUMENTS

| | | | |
|---|---|---|---|
| 2,902,146 | 9/1959 | Doherty | 128/759 X |
| 3,438,366 | 4/1969 | Kariher et al. | 128/757 |
| 3,512,518 | 5/1970 | Mishkin et al. | 128/759 X |
| 3,513,830 | 5/1970 | Kalayjian | 128/759 |
| 3,777,743 | 12/1973 | Binard et al. | 128/305 X |
| 3,800,781 | 4/1974 | Zalucki | 128/749 |
| 3,961,620 | 6/1976 | Schack et al. | 128/304 X |
| 4,338,952 | 7/1982 | Augros | 128/757 |

Primary Examiner—Edward M. Coven
Attorney, Agent, or Firm—Witherspoon & Hargest

[57] ABSTRACT

The present invention relates briefly to a sampling instrument for simultaneously drawing of cell-samples and bacteriological samples, preferably from the uterus of animals. The instrument comprises a lead-in tube (2) and an operating rod (3), the samplers (5, 6) being secured to the operating rod. The samplers are a cell-sampler (5) at the leading-in end of the operating rod and a bacteriological sampler (6) on the rod a distance inwards of the cell-sampler (5). Normally, both the samplers (5, 6) are located within the tube (2). The lead-in tube (2) acts on one hand as an aid for the insertion of the samplers (5, 6) and on the other hand as a protection therefore both during the storing of the instrument as well as after sample drawing. Due to the fact that the samplers easily may be separated from the rest of the operating rod and the tube (2) easily is cut into convenient portions and closed at the ends thereof enclosing one or both of the samplers there is obtained an easily transportable capsule which protects the sample from the environment and vice versa.

8 Claims, 2 Drawing Figures

U.S. Patent   Jan. 7, 1986   4,562,847

INSTRUMENT FOR OBTAINING SAMPLES FROM UTERUS OF ANIMALS

The present invention relates to sampling instruments especially for sampling from the endometrium of the uterus wall, as well as, for example, from the air-passages of animals, and more particularly to a disposable sampler for simultaneous sampling of cell-samples as well as bacteriological samples.

The sampling of cell-samples from the endometrium of animals is mostly intended to find out the occurrence of leucocytes, although there may be other reasons for sampling. In accordance with the state of the art, such sampling takes place by the aid of a scraping device which is inserted into the uterus and onto which samples of the cells adhere. In U.S. Pat. Nos. 3,777,743 and 3,961,620 there are shown examples of such scraping devices which, however, are intended to be used for sampling from women. It is also known to sample bacteriological samples from a uterus by suction of samples of fluid therefrom.

An encroachment into the uterus as well as into the air-passages for sampling constitutes a risk for the animal from which the sample is taken as well as for the operator. For the animal the risk is inherent in the imperfect sterilization of the instrument as well as in the imperfect function thereof. The surrounding conditions are not favourable from the sterilizing point of view and accordingly it is very important that the number of samples be kept as small as possible and that they be as lenient as possible.

Instruments of the type to which the present invention refer include a hose or tubular insertion portion having a length of at least 50 centimeters or more, and a diameter of one or a few centimeters. Such parts are very difficult to sterilize on the one hand due to the length thereof which requires big autoclaves and on the other hand due to the fact that the internal cleaning is difficult to carry out. A badly sterilized instrument may of course give rise to an infection of the animal from which the sample is taken but the great risk is the fact that the taken sample gives an incorrect result with the problems resulting therefrom.

After the sampling it is also important that the samples are not subjected to impurity sources which might affect the results of the analyses. In addition, they must be kept so that they cannot infect the surroundings such as the operator.

If it is possible to observe, for example, leucocytes from a scraped sample from the endometrium such is an indication of existing infection. In connection with prior art sampling devices it has been necessary to make a new encroachment for taking a bacteriological sample in order to determine the art of infection, sometimes due to the fact that the first sample has been incorrect for reasons previously mentioned.

The object of the present invention is to remove the above mentioned problems and to win some other advantages. This object is reached by a sampling instrument of the type referred to in the claims from which also the features especially characterizing the invention are clear.

Figure 2:
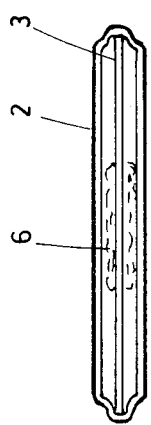

The invention is more fully described herein in the following in connection with the attached drawing in which FIG. 1 is a schematical partly cut longitudinal section through a sampling instrument in accordance with the invention, and FIG. 2 is a broken longitudinal section through a portion of the sampling instrument shown in FIG. 1.

The sampling instrument 1 consists of a tube 2 of synthetic material and of a length of between 50 and 100 centimeters. The tube 2 is stiff but permits some bending so that without difficulties it can be inserted into e.g. an uterus without being compressed. A rod 3 is extended through the tube 2, the rod preferably being of the same material as the tube 2 and having the same stiffness and bending characteristics as the tube. The rod 3 is essentially longer than the tube 2.

At the outer or operating end of the rod 3 is provided a button 4 which on the one hand facilitate the operation of the rod 3 and on the other hand prevents the rod from disappearing into the tube 2. At the other or sampling end, there is attached a cell-sampler 5, and a short distance therefrom there is attached a bacterial sampler 6 at the rod 3. In the starting position said samplers 5 and 6 are located within the tube 2.

The cell sampler 5 is in the form of a scraping means having edges or irregularities suitable for catching cells on, for example the endometrium. In the shown and preferred embodiment the cell-sampler 5 is of circular cross-section and is provided with a number of peripheral grooves whereby a number of edges 7 is formed. When the cell-sampler 5 is brought into contact with the endometrium or corresponding wall and is drawn therealong cells are caught by said edges 7 and are collected in the grooves.

The bacterial sampler 6 is attached to the rod 3 so close to the cell-sampler 5 that during the cell-sampling the sample 6 will also touch the endometrium. The bacterial sampler 6 consists of a porous wet absorbing material such as cotton which absorbs the secretion that is in the uterus.

Before the sampling, the sampling instrument 1 is packed in a sterilized condition in a hermetically closed plastic casing. Said casing is broken immediately before taking the sample. Then the tube 2, having the samplers 5 and 6 located therein on rod 3 as shown in FIG. 1, is inserted into the uterus through the vagina and the cervix channel. In this position the operating rod 3 is moved inwardly so that the cell-sampler 5 as well as the bacterial sampler 6 are brought into contact with the endometrium. Having been turned some revolutions and been drawn towards and backwards a short distance the two samplers 5 and 6 are drawn back into the tube 2 to the original position and at least so far that they are safely located within the tube 2. After that the sampling instrument is withdrawn from the uterus and the animal.

In connection with the sampling carried out in this way there is no risk of spreading infections by the instrument when outside the uterus. If the analyses of the samples are to be carried out later on and not in connection with the sampling the sampling instrument may be placed in the broken package whereby the sampler is well protected until it is time for carrying out the analyses.

When the analysis is to be carried out the cell-sampler 5 is moved out of the tube 2 and is separated from the operating rod 3. The separation can be carried out by cutting the rod 3 by the aid of a tool, by breaking or preferably by burning. If in connection with microscopy there is observed signs indicating an infection then the bacterial sampler 6 is sent to a laboratory for determining which type of infection is in question.

When separating the rod 3 by burning which might take place by the air of a common cigarette lighter the adjacent end of the tube 2 is simultaneously melted to a hermetical seal. It is preferred to separate the tube 2 and the rod 3 on the other side of the bacterial sampler 6 in connection with the same operation so that also the other end of the tube 2 is hermetically sealed. The result is that the bacterial sampler 6 is housed in a piece of tube as is clear from FIG. 2.

There are of course other possibilities of closing the piece of tube in accordance with FIG. 2 depending upon the cutting of the tube 2. Hence, there may be cutting marks in the tube 2 as well as in the rod 3 and the sealing may then be carried out by the aid of plugs and the like or by applying adhering tapes over the open tube ends.

In order to facilitate the opening, of the piece of tube containing the bacterial sampler 6 in the laboratory there is preferably a cutting mark in the tube 2 in the portion thereof surrounding the bacterial sampler 6. Accordingly, the laboratory staff may then easily break the tube 2 at the mark in order to be able to release the bacterial sampler 6 for the following analysis.

Keeping the bacterial sampler 6 hermetically closed in a piece of tube in the way just mentioned is advantageous in that it may be put into an envelope or into a bag and without any risk be sent to laboratories even by common post.

In an alternative embodiment the complete sampling instrument 1 is enclosed in a tight casing of a thin plastic sheeting. Outside the tight casing there is a hermetically enclosed plastic covering which constitutes the package itself and which is broken when the sampling instrument is to be used. The internal casing covers the sampling instrument 1 in an unbroken condition during the insertion of the instrument through the vagina and a distance into, if not completely through, the cervix channel. In this inserted position the tube 2 is allowed to break through the casing whereafter the sampling is carried out in the way previously described.

Having carried out the sampling, the tube 2 enclosing the samplers 5 and 6 is retracted into the casing whereafter the complete sampling instrument 1 is removed and treated in the way previously mentioned.

The advantage obtained by using a casing of the type just mentioned is the fact that that sampling instrument can be kept in a sterile condition until the casing is broken. Accordingly, the samples drawn from the uterus cannot be affected by any infection or other condition within the vagina which could give rise to an incorrect sampling result. Without such a protecting casing there is a little risk that the leading end of the tube 2 during the insertion of the sampling instrument will catch secretion or the like which during the sampling might introduce an infection into the uterus and affect the sample drawn from the uterus.

It is clear from the above that a sampling instrument has been obtained which removes the drawbacks mentioned in the preamble and residing in prior type sampling instruments. Simultaneously advantages have been obtained with regard to the handling of the taken samples.

We claim:

1. A sampling instrument of disposable type for simultaneous sampling of cell samples and bacteriological samples from the uterus of animals comprising a flexible tube, a rod having an operating end extending outside of said tube and a sampling end extending inside of said tube, said rod being moveable relative to said tube in such a manner that said sampling end can be reciprocated out of and back into said tube, and means attached to said sampling end for taking a first cell sample from said uterus when said tube is inserted into said uterus and said sampling end is moved out of said tube a first distance, subsequently taking a second distinct bacteriological sample from said uterus when said sampling end is moved out of said tube an additional second distance, and for allowing said first and second samples to be moved back into said tube prior to the removal of said tube from the uterus.

2. The sampling instrument of claim 1 wherein said rod includes one or more cutting masks for separating one or more of said samplers from said rod.

3. The sampling instrument of claim 1 wherein said tube includes one or more cutting marks for separating the portion of said tube, enclosing one or more of said samplers, from the remaining portion of said tube.

4. The sampling instrument of claim 3 wherein said rod includes one or more cutting marks fracture for separating one or more of said samplers from said rod.

5. The sampling instrument of claim 3 wherein said tube includes a cutting mark in the portion thereof surrounding said bacteriological sampler.

6. The sampling instrument of claim 4 wherein said tube includes a cutting mark in the portion thereof surrounding said bacteriological sampler.

7. The sampling instrument of claim 2 wherein said tube includes a cutting mark in the portion thereof surrounding said bacteriological sampler.

8. The sampling instrument of claim 2 wherein said instrument is enclosed within a casing of sheet material which is hermetically closed.

* * * * *